United States Patent [19]

Beckwith et al.

[11] Patent Number: 4,946,783

[45] Date of Patent: Aug. 7, 1990

[54] PERIPLASMIC PROTEASE MUTANTS OF ESCHERICHIA COLI

[75] Inventors: Jonathan R. Beckwith, Cambridge; Kathryn L. Strauch, Brighton, both of Mass.

[73] Assignee: President and Fellows of Harvard College, Cambridge, Mass.

[21] Appl. No.: 85,402

[22] Filed: Aug. 14, 1987

Related U.S. Application Data

[63] Continuation-in-part of Ser. No. 9,233, Jan. 30, 1987, abandoned.

[51] Int. Cl.$^5$ .................... C12N 15/00; C12N 1/20
[52] U.S. Cl. ........................ 435/172.1; 435/172.3; 435/252.33; 435/252.8; 435/849; 935/14; 935/29; 935/48; 935/73
[58] Field of Search ............ 435/172.1, 172.3, 252.8

[56] References Cited

PUBLICATIONS

Nakata, *Escherichia coli* Mutants Deficient in the Production of Alkaline Phosphatase Isozymes, J. Bacteriology, vol. 134, pp. 287–294 (Apr. 1978).
Suzuki, et al., Murein–Lipoprotein of *Escherichia coli*: A Protein Involved in the Stabilization of Bacterial Cell Envelope, Molec. gen. Genet 167, pp. 1–9 (1978).
Cheng, et al., Purification and Characterization of Protease III from *Escherichia coli*, J. Biological Chem., 254 pp. 4698–4706 (1979).
Lazdunski, Purification and Properties of a Periplasmic Aminoendopeptidase from *Escherichia coli*, Eur. J. Biochem., 60, 363–369 (1975).
Inouye et al., Cloning and Restriction Mapping of the Alkaline Phosphatase Structural Gene (phoA) of *Escherichia coli* and Generation of Deletion Mutants In Vitro; J. Bacteriology vol. 146, pp. 668–675 (1981).
Swamy et al., Subcellular Distribution of Various Proteases in *Escherichia coli*, J. of Bacteriology, 1027–1033 vol. 149 3:1027–1033 (Mar. 1982).
Kumamoto, Evidence for Specificity at an Early Step in Protein Export in *Escherichia coli*, J. of Bacteriology, vol. 163, pp.267–274 (Jul. 1985).
Cheng, et al., Isolation and Characterization of Mutations in the Structural Gene for Protease III (ptr), J. of Bacteriology, vol. 140, pp. 125–130 (Oct. 1979).
Manoil et al., TnphoA: A Transposon Probe for Protein Export Signals, Proc. Natl. Acad. Sci U.S.A., vol. 82, pp. 8129–8133 (Dec. 1985).
Lopes et al., Leakage of Periplasmic Enzymes by Mutants of *Escherichia coli* and *Salmonella typhimurium*: Isolation of "Periplasmic Leaky" Mutants, J. Bacteriology, pp. 520–525 (Feb. 1972).
Manoil et al., A Genetic Approach to Analyzing Membrane Protein Topology, Science vol. 233, pp. 1403–1408 (Sep. 1986).
Palmer et al., Journal of Bacteriology, vol. 169, Characterization of a Membrane–Associated Serine Protease in *Escherichia coli*, pp. 1474–1479, (1987).
Ichihara et al., "Protease IV, A Cytoplasmic Membrane Protein of *Escherichia coli*, Has Signal Peptide Peptidase Activity", The Journal of Biological Chemistry, vol. 259, No. 15, Issue of Aug. 10, pp. 9853–9857, 1984.
Suzuki, et al., "Characterization of the sppA Gene Coding for Protease IV, A Signal Peptide Peptidase of *Escherichia coli*", Journal of Bacteriology, Jun. 1987, pp. 2523–2528, vol. 169, no. 6.

*Primary Examiner*—Thomas Mays
*Attorney, Agent, or Firm*—Fish & Richardson

[57] ABSTRACT

This invention features a method of isolating a mutant strain of *Escherichia coli*, having a defective periplasmic protease, the method comprising the steps of: mutagenizing an *E. coli* cell, wherein the cell comprises: (a) an inner and an outer membrane, (b) a periplasmic space between the membranes, (c) a protein which in a first state is mobile, being able to move through the outer membrane and enter medium surrounding the cells, the protein in the first state being detectable in the medium, and in a second state is not mobile, remaining inside the cell, and (d) a periplasmic protease which converts the protein from the second state to the first state in the cell, and selecting a mutant cell which produces a reduced level of the detectable protein in the medium compared to the *E. coli* cell, wherein the mutant cell comprises the defective periplasmic protease.

This invention also features mutant strains of *E. coli* having a defective periplasmic protease.

20 Claims, 2 Drawing Sheets

4,946,783

PERIPLASMIC PROTEASE MUTANTS OF ESCHERICHIA COLI

The work described in this application was supported in part by funding from the N.I.H., specifically by grant No. GM 09843 03 and the U.S. Government has certain rights in this invention.

BACKGROUND OF THE INVENTION

This application is a continuation in part of U.S. Ser. No. 9233, filed Jan. 30, 1987, now abandoned.

This invention relates to mutants of *Escherichia coli* having defective proteases.

Proteases in *E. coli* are enzymes which cleave certain proteins to produce lower molecular weight products. Such proteases have several functions. For example, they are involved in the destruction of abnormal or foreign proteins, protein excretion, protein turnover during starvation, and inactivation of functional or regulatory proteins. Cheng et al., 254 J. Biol. Chem. 4698, 1979. In addition, proteases play critical roles in processing of secretory and membrane proteins, the utilization of exogenous peptides, and (from a more practical viewpoint) in the rapid intracellular degradation of cloned foreign peptides expressed in *E. coli.* Swamy et al., 149 J. Bacteriol. 1027, 1982.

Proteases are found in one or more subcellular compartments in *E. coli*, including the cytoplasm and the periplasmic space. The periplasmic space is the region between the inner and outer membranes of *E. coli.* Functionally, proteases in the periplasmic space are defined as those proteases which are present in the periplasmic fraction of *E. coli* prepared by the method of Nossal et al., 241 J. Biol. Chem. 3055, 1966 or Neu et al., 240 J. Biol. Chem. 3685, 1965. Briefly, these methods involve releasing enzymes from the periplasmic space by osmotically shocking exponentially growing cells. Swamy et al., supra, describe finding protease Pi (or III), and Mi, almost exclusively in the periplasmic space; whereas proteases Do and Re are found in both this region and in the cytoplasm. Protease III preferentially degrades proteins of molecular weight less than 7 kD.

Mutant strains having a defective protease III have been isolated by Cheng et al. 140 J. Bacteriol. 125, 1979. These were isolated by heavy mutagenesis of *E. coli* cells and subsequent screening for decreased enzymatic activity.

SUMMARY OF THE INVENTION

In one aspect, the invention features a method of isolating a mutant strain of *E. coli*, having a defective periplasmic protease, the method comprising the steps of: mutagenizing an *E. coli* cell, wherein the cell comprises (a) an inner and an outer membrane, (b) a periplasmic space between the membranes (c) a protein which in a first state is mobile, being able to move through the outer membrane and enter medium surrounding the cell, and in this state is detectable in this medium, and in a second state is not mobile, remaining inside the cell and (d) a periplasmic protease which converts the protein from the second state to the first state in the cell; and selecting a mutant cell which produces a reduced level of the detectable protein in the medium compared to an unmutagenized *E. coli* cell.

In preferred embodiments, the protein is detected by (a) measuring the enzymatic activity of the protein in the medium, or (b) detecting reactivity of the protein in the medium with a specific antibody to the protein; the selecting step comprises screening a plurality of mutagenized cells by culturing the cells and testing each resulting culture or colony for a lower level of protein in the medium compared to a culture produced from a non-mutagenized cell; the protein comprises a fusion of a first polypeptide chain, which is susceptible to proteolysis by the periplasmic protease, and a second polypeptide chain which has a readily detectable enzymatic activity and is not proteolysed by the protease; the first polypeptide chain is a portion of Tsr, wherein this portion comprises at least 20 amino acids; the second polypeptide chain comprises a portion of alkaline phosphatase from *E. coli;* the half-life of the protein in the second state is less than 60 minutes in a cell having a normal protease, and the half life is greater than 60 minutes in the cell having a defective protease; the protein in the second state is bound to one cell membrane; and the cell comprises a mutation resulting in the cell allowing the protein to move through the outer membrane of the cell.

In a second aspect the invention features a mutant strain of *E. coli* having a defective periplasmic protease, wherein the protease acts on proteins of at least 10 kD and is active at protein sites at least 30 amino acids from the amino terminus of the protein.

In preferred embodiments the strain is isolated by mutagenizing an *E. coli* cell, wherein the cell comprises an inner and an outer membrane, a periplasmic space between the membranes, a protein which in a first state is mobile, being able to move through the outer membrane and enter medium surrounding the second cell, the protein in this first state being detectable in the medium, and in a second state is not mobile, remaining inside the cell, and a periplasmic protease which converts the protein from the second state to the first state in the cell, and selecting a mutant cell which produces a reduced level of the detectable protein in the medium, compared to the non-mutagenized *E. coli* cell wherein the mutant cell comprises the defective periplasmic protease; most preferably the mutant cell is strain K4.

In a third aspect, the invention features a cell having a mutation in a gene encoding a periplasmic protease, wherein the gene is located within 1 minute of the K4 mutation and the mutation reduces the level of activity of that protease.

In preferred embodiments the gene is linked by P1 transduction to *pan* or *fhu*AB (*ton*A), and is located near a map position of four minutes on the *E. coli* chromosome; the gene is present on the plasmid pKS12, contained in deposit 67488; the mutation is a deletion mutation, most preferably it is a deletion of a part of deqP, even more preferably it is deqP41 or deqP44.

In a fourth aspect, the invention features a method for isolating a mutant strain of *E. coli*, having a defective periplasmic protease. The method comprises the steps of cloning a gene fragment encoding a part of the protease, and deleting the fragment from the *E. coli* strain.

This invention provides a procedure for isolating mutants having mutations that reduce or prevent proteolytic breakdown of proteins in the periplasmic space. The existence of such mutants is particularly useful for enhancing the expression of foreign proteins in *E. coli*, since it is these proteins which are frequently degraded in bacterial cells.

Other features and advantages of the invention will be apparent from the following description of the preferred embodiments thereof and from the claims.

DESCRIPTION OF THE PREFERRED EMBODIMENTS

The figures will first briefly be described.

DRAWINGS

STRUCTURE

In general, the method of this invention proteases by detecting cells which have a decreased ability to secrete a detectable protein.

Periplasmic Protease

In general, a periplasmic protease is an enzyme which can be found in the region between the inner and outer membranes, and/or is present in the periplasmic fraction isolated as described above. This term also includes proteases found in the membrane fractions of cells. The protease may be present in the cytoplasm as well as the periplasm, and may be soluble or attached to one of the membranes. These proteases will degrade proteins in the periplasmic fraction, or in the part of the inner or outer membranes facing the periplasm.

Preferably, the protease activity is characterized in that it will cleave a polypeptide chain at a point greater than about 20 to 30 amino acids from the amino terminus. Thus, for example, it is not simply a signal sequence protease which removes a secretory sequence from a polypeptide. In addition, the protease preferably acts on proteins of greater than 10 kD, (e.g., Tsr, as described below) and may act on small proteins too.

Detectable Protein

A detectable protein is one which can be readily detected when released from a cell. For example, it may have a specific enzymatic activity for which a routine test can be devised, e.g., alkaline phosphatase, or it may form a specific antigen which can be detected by use of a labelled or unlabeled antibody, or by other chemical or biochemical methods of detecting specific proteins. The protein must not lose this property in the presence of a periplasmic protease. The protein is normally relatively non mobile within the periplasmic region, that is it can only rarely leave the periplasmic region. However, it is converted by a periplasmic protease to a mobile form which is able to leave the periplasmic region.

This protein may be a naturally occurring protein or one formed by recombinant DNA techniques. It may be expressed from a cloning vector or from chromosomal DNA.

Methods

Figure 1:
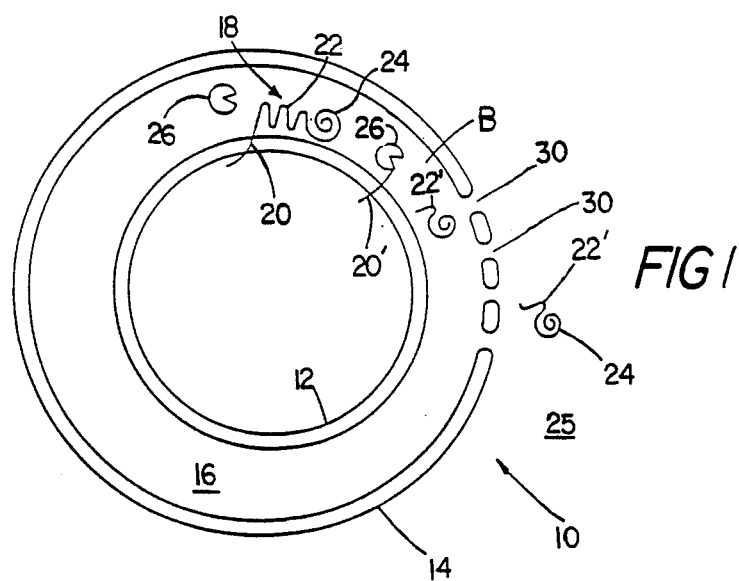
FIG. 1 is a diagrammatic representation of the periplasmic region in *E. coli* and the action of a protease on a protein in this region.

The general method of the invention features mutagenesis of a cell shown in FIG. 1. Referring to FIG. 1, cell 10 has an inner membrane 12 and an outer membrane 14 defining a periplasmic region 16. Within this region is a detectable protein 18 having an integral membrane portion 20, and a soluble portion 22 including a detectable portion 24. Protein 18 is susceptible to proteolysis by periplasmic protease 26 which cleaves protein 18 into at least two parts, soluble portion 22' and membrane portion 20', shown at B in FIG. 1. Soluble portion 22' is thus mobilized and able to leave cell 10 via regions 30 in outer membrane 14. Regions 30 may be naturally occurring passages in membrane 14, or may be created by mutations within the cell, e.g., the mutation in a lipoprotein mutant strain causing the to be deficient in membrane lipoprotein. Mobile portion 22' retains detectable portion 24 and can be detected as it diffuses into medium 25 surrounding cell 10.

Figure 2:
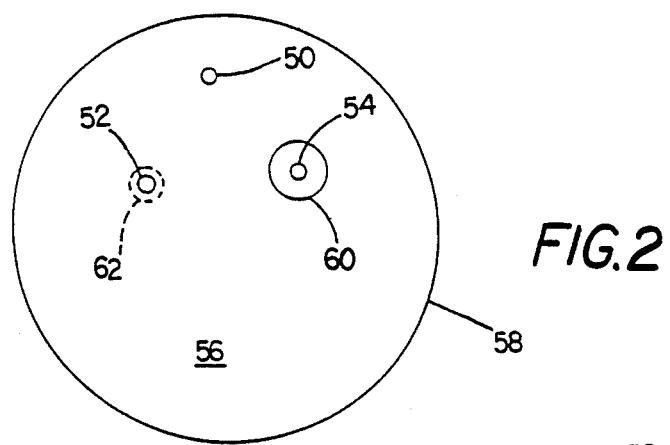
FIG. 2 is a diagrammatic representation of the appearance of mutant and normal (or wild type) *E. coli* colonies using one method for detecting protease defective cells.

Referring to FIG. 2, mutant strains can be detected by using a plate test. Colonies 50, 52, and 54 of potential mutant strains are grown on appropriate media 56 in Petri dish 58 containing chemicals suitable for producing a detectable reaction with detectable portion 24 of mobile or soluble portion 22'. If no mutation is present in a gene in the cell affecting periplasmic protease activity then detectable protein 24 is observed as a large halo 60, shown around colony 54 (a wild-type reaction). If there is a mutation in a periplasmic protease gene in the strain then the halo may be reduced as shown in halo 62, or non existent, as shown in colony 50. That is, the mutation affects the ability of protease 26 in FIG. 1 to cleave protein 18 as shown at B.

The mutant strains so isolated may have mutations in the structural gene encoding the periplasmic protease, in a regulatory region, or in a gene controlling expression of the protease. Once isolated, the mutation can be mapped by standard procedures, the gene involved cloned, and further mutations constructed by standard techniques, such as in vitro mutagenesis of the cloned DNA, or by construction of deletion mutants. If a genetic locus is involved, i e., a DNA region encoding more than one structural gene affecting periplasmic protease activity, then mutations in genes surrounding the isolated mutation will also be useful, e.q., mapping up to 1 minute from the original mutation point.

EXAMPLE 1

ISOLATION OF PERIPLASMIC PROTEASE MUTANTS

Figure 3:
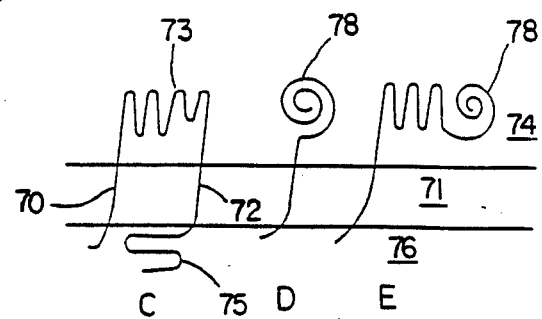
FIG. 3 is a diagrammatic representation of the location of Tsr and fusion proteins in an *E. coli* inner membrane.

Referring to FIG. 3 inner membrane 71 is shown separating periplasmic region 74 and cytoplasm 76. C represents Tsr which is a protein in *E. coli* involved in chemotaxis. Tsr has two membrane-spanning stretches 70, 72 separating two soluble domains 73, 75, one in the periplasm 74, one in the cytoplasm 76. Manoil et al. 233 Science 1403, (1986). Two gene fusions of alkaline phosphatase and Tsr, encoded by plasmids pCM204 and pCM203, were constructed as described in Manoil et al., supra to produce protein fusions in which alkaline phosphatase moiety extends into the periplasmic region. The kanamycin resistance factor in these plasmids was removed by standard technique, to produce pKS1 and pKS3 respectively. These fusions were utilized in the following experiments. In one, D of FIG. 3, alkaline phosphatase 78 is fused near to the first membrane-span ning segment 70 (fusion 1) and yields a hybrid protein of about 49 kD molecular weight. This protein is membrane bound, proteolytically stable and immunoprecipitable with antiserum to alkaline phosphatase. Fusion 2, shown as E in the FIG. 3, consists of alkaline phosphatase 78 fused to the end of the large periplasmic domain 73 of Tsr. This fusion produces a hybrid protein of about 70 kD which is unstable in vivo, exhibiting a half life of about 15 minutes. As the 70 kD protein is degraded, a stable 47 kD polypeptide accumulates which is immunoprecipitable by antiserum to alkaline phosphatase. The 70 kD protein is membrane bound, whilst the 47 kD polypeptide is soluble, and located in the periplasmic region. The alkaline phosphatase 78 in the 47 kD polypeptide is enzymatically active.

These Tsr alkaline phosphatase fusions are carried on a high copy pBR322 derivative conferring ampicillin resistance. In order to make strains containing fusions 1 or 2 leaky to alkaline phosphatase, the fusions are introduced into a strain having a mutation which eliminates expression of lipoprotein, e.g., lpp5508, Suzuki et al. 167 Mol. Gen. Genet. 1, 1978. Lipoprotein interacts with the outer membrane via covalently attached lipid. This lipid inserts into the bilayer of the outer membrane and is covalently linked to the peptidoglycan located in the periplasmic space. In the absence of lipoprotein the outer membrane structure is altered and periplasmic proteins are partially released to the surrounding medium. In otherwise wild-type cells, about 25% of alkaline phosphatase is released into the medium, compared to less than 1% for wild type E. coli strains. Such mutants have been described by Lopes et al., 104 J. Bacteriol. 520, 1972, and Suzuki et al. supra.

The two resulting strains are distinguishable after replica plating to Luria broth agar plates containing XP (5-bromo-4-chloro-3-indolyl-phosphate, 100–200 μg/ml), a histochemical stain for alkaline phosphatase, hydrolysis of which yields a blue product. Cells containing some soluble alkaline phosphatase exhibit a blue halo around the colony due to diffusion of the polypeptide into the medium. Cells with only membrane-bound or non-mobile enzymes have halo. Fusion 1-containing colonies produce colonies with a very small halo (less than 1 mm), whilst fusion 2-containing colonies produce a distinctly larger halo (approx. 3 mm).

A strain containing fusion 2 was checked for its ability to produce a halo on XP medium. The strain was then treated with ethylmethane sulfonate (EMS) or with Tn5 (selecting kanamycin resistance) to cause mutations using standard procedures. The surviving colonies were then replica plated onto the above described XP media and screened for those which produce a reduced halo, or no halo.

Colonies having a smaller halo of XP hydrolysis represent colonies having mutations causing either (a) a reduced proteolysis of the fusion protein, leading to a reduced proportion of alkaline phosphatase activity in the soluble mobile form, or (b) a reduced level of expression of fusion protein, leading to lower total alkaline phosphatase activity. Four mutant strains having reduced halos were isolated, and their respective mutations named 1-1, 4-1 (both from EMS mutagenesis) or K4, K16 (from Tn5 mutagenesis).

In order to determine if these mutations caused a reduced proteolytic activity the relative amounts of alkaline phosphatase activity in the membrane bound and the soluble form was determined. The above strains were subjected to a cold osmotic shock procedure to release periplasmic proteins from the cells (Neu et al., supra). The shock fluid (periplasm) and cell pellet (membranes and cytoplasm) were separated by centrifugation and the alkaline phosphatase activity in each fraction assayed (see Table 1).

The strain expressing Fusion 1 had 90% or more of the alkaline phosphatase activity in the pellet. Cells expressing Fusion 2 had only 25% of the alkaline phosphatase activity in the pellet. The two strains containing derived from the EMS mutagenesis procedure of cells expressing fusion 2, 1-1 and 4-1, had approximately 70% of alkaline phosphatase activity in the pellet. One Tn5 insertion mutant, containing mutation K4, had 90% or greater alkaline phosphatase in the pellet, and another, containing mutation K16, had 85% of the alkaling phosphatase in the pellet. These four mutant strains appear to have mutations which have altered the proteolytic breakdown of the Tsr-alkaline phosphatase Fusion 2, and thus the cellular location of alkaline phosphatase.

TABLE 1

| | Location of Alkaline Phosphatase Activity | | | |
|---|---|---|---|---|
| Protease Genotype of Host Strain | Tsr-Alkaline Phosphatase Fusion on Plasmid | % Alkaline Phosphatase in Membrane | % Alkaline Phosphatase in Periplasm | Half-Life of Protein |
| wild type | 1 | 95 | 5 | |
| wild-type | 2 | 25 | 75 | 15 minutes |
| 1-1 | 2 | 70 | 30 | 30 minutes |
| 4-1 | 2 | 70 | 30 | 30 minutes |
| K4 | 2 | 95 | 5 | >60 minutes |
| K16 | 2 | 85 | 15 | >60 minutes |

Proteolysis of Fusion 2 in these mutant strains was assayed directly by pulse labelling the cellular proteins with $^{35}$S-methionine, followed by chase with unlabeled methionine for one hour. The Tsr-alkaline phosphatase hybrid and its breakdown product were immunoprecipitated with antiserum to alkaline phosphatase, the polypeptides separated by SDS-polyacrylamide gel electrophoresis, and visualized by fluorography. The amount of radioactivity in the hybrid protein and the breakdown product was quantitated by cutting the radioactive polypeptides out of the gels, treating them with a tissue solubilizing reagent and subjected them to scintillation counting.

In strains carrying mutations 1-1 and 4-1 the 70 kD Tsr-alkaline phosphatase hybrid had a half life approximately twice as long (30 minutes) as in wild-type cells (15 minutes) and the 47 kD breakdown product accumulated at a slower rate. In strains carrying mutations K4 and K16 there was no detectable loss of the 70 kD hybrid or accumulation of the 47 kD product. The proteolytic breakdown of the Tsr-alkaline phosphatase hybrid is reduced or eliminated in these mutant strains.

Other proteins were tested as substrates for the mutated periplasmic proteases. These proteins include two fusions of maltose-binding protein (MBP) and alkaline phosphatase (with MBP fused to alkaline phosphatase at about amino acid 230 or 270 respectively, by the method described by Manoil et al. supra), a β-lactamase alkaline phosphatase fusion (Manoil et al., 82 Proc. Natl. Acad. Sci. 8129, 1985). The fusions were assayed with antibody to alkaline phosphatase. Strains containing mutation K4 stabilize the breakdown of all 3 proteins listed above, whilst mutation K16 stabilizes only the Tsr-alkaline phosphatase fusion. The K4 mutation also stabilizes two internally deleted MBP proteins, deleted for amino acids 57-145 or 142-150 (this protein was assayed using an antibody to MBP).

It has been shown, as described above, that a strain producing a detectable protein is useful for isolating periplasmic protease mutants. Other strains producing the same or equivalent protein will be similarly useful. In order to produce other mutant strains having mutations in the same or different protease genes to those already isolated, the above described procedures can simply be repeated. That is, any strain which is leaky to periplasmic proteins can be transformed with a vector encoding a protein having properties similar to protein fusion 2, mutagenized by any standard technique and the desired mutants screened for, as described above, or by an equivalent technique. For example, the plasmid in the strain having the mutation K4 (strain KS334, which contains the Tsr-alkaline phosphatase fusion 2 encoded by pKS3, deposited as described below) may be isolated and used to transform one of the strains described by Lopes et al., supra, or Suzuki et al., supra, selecting ampicillin resistance, and used for production of protease mutants.

Use

The protease genes in which the above mutations are located, and any other genes which are detected in future routine experiments can be located genetically by standard mapping procedures. The genes and their mutations can then be cloned and other mutations created in vitro. These mutated genes can then be introduced into any commercially important *E. coli* strain being used for production of a protein which is susceptible to the normal protease activity. The level of protein production should thereby be enhanced.

For example, useful genetic characterization of the genes controlling periplasmic proteases will involve (1) determining the number of loci at which mutations occur, (2) mapping the genes, (3) cloning the genes into vectors, (4) isolation of null mutations in the genes, and (5) identification of the gene product of each locus. To clone the genes, vector libraries of wild type cells can be made by standard technique. The vectors can be introduced into a mutant strain deficient in breakdown of the Tsr alkaline phosphatase hybrid and the resulting strains can be tested for production of alkaline phosphatase halos around colonies (indicating that the plasmid has restored breakdown of the Tsr alkaline phosphatase hybrids). Once the gene has been cloned, Tn insertions into the plasmid are readily screened for those which inactivate the proteolysis function located on the plasmid. Such inactivated genes can then be introduced into any desired strain.

EXAMPLE 2

MAPPING OF DEG P

The K4 mutation is referred to as degP4::Tn5, indicating that Tn5 is inserted into the degP gene.

Since Tn5 has a high frequency of transposition during Hfr matings, a Tn10 insertion (having a lower frequency of transposition than Tn5), cotransducible by P1 phage with deg P4::Tn5 was isolated by standard methods, as described by Davis et al. Advanced Bacterial Genetics, Cold Spring Harbor Laboratory, Cold Spring Harbor, NY 11724, 1980. This Tn10 insertion (zad-340::Tn10) was then mapped as follows, using standard procedures.

zad-340::Tn10 was introduced into Hfr strains by P1 transduction. Hfr matings were carried out to determine which Hfr's with particular origins of transfer at different regions of the chromosome can transfer the Tet$^r$ of Tn10 at highest frequency. Those Hfr's with high levels of transfer have the Tn10 close to the origin of transfer. Hfr's (HfrH, generating counterclockwise transfer from 97 minutes, and HfrP4, generating clockwise transfer from 7 minutes) which transfer the Tn10 at high frequency were used for time of entry experiments. Auxotrophic markers near the origin of transfer were selected and the linkage of Tet$^R$ to those markers determined.

Markers which appeared close to the Tn10 in Hfr crosses were used in P1 transductions (Miller, Experiments in Molecular Genetics, Cold Spring Harbor Laboratory, Cold Spring Harbor, N.Y. 1972) to measure linkage of those markers to deqP4::Tn5. The results are shown in Table 2. The markers used were (a) pan, which is a gene involved in pantothenic acid biosynthesis; mutants having a defective pan gene require this vitamin for growth; and (b) fhuAB (tonA) which is a gene involved with an iron transport system containing an outer membrane protein which is a receptor for several bacteriophages (T1, T5, and $\phi$80); mutants having a defective fhuAB gene are resistant to these phages. These genes are located at 3.4 and 3.7 minutes on the *E. coli* chromosome (Bachman, 1983 Linkage Map of *E. coli* K, *Microbiological Reviews* 47: 180. The percent cotransfer of the wild type alleles with Tn5 (encoding Kan$^R$) was measured. These data indicate that deqP is located near to the four minutes position on the *E. coli* map.

TABLE 2

| Donor | Recipient | % Linkage |
|---|---|---|
| degP4::Tn5 | pan | 19 $\frac{(19\ Pan^+)}{100\ Kan^r}$ |
| degP4::Tn5 | pan | 17 $\frac{(16\ Pan^+}{97\ Kan^r}$ |
| degP4::Tn5 | fhuAB(tonA) | 74 $\frac{(132\phi 80^s}{175\ Kan^r}$ |

EXAMPLE 3

Cloning of deqP deqP4::Tn5 has two phenotypes: In an lpp-(lipoprotein deficient) mutant and in the presence of pKS3 (encoding Tsr AP2 fusion protein) the mutant does not leak alkaline phosphatase (AP) to medium and does not exhibit a blue halo on XP medium; in an lpp- and malT$^c$ (a mutation which causes constitutive expression of genes for utilization of maltose) mutant the deqP4 mutant grows very poorly at 42° C. on rich (tryptone yeast extract) medium. Growth is poor enough to score DegP-by colony size, or by replica plating of colonies.

Plasmid libraries were prepared by the method of Groisman et al. 81 *Proc. Nat. Acad. Sci., USA* 82 1480, 1984. The starting vector plasmid was pEG109 (Mud4042: :phoA+proC)). Since the presence of phoA on this plasmid makes it difficult to assay the DegP phenotype two plasmids. pKS5 and pKS8, (both Mud4042: :proAB) were isolated, as described by Groisman, supra. These plasmids were used to produce chromosomal libraries. The libraries were introduced into a ΔphoA lpp-5508 malT$^c$1 deqP4::Tn5 (Mu ) strain (KS419), selecting chloramphenicol resistance (Cam$^r$)

and growth at 42° C. Thus, only those bacteria having a plasmid encoding Cam$^r$ and able to complement the deqP mutation will grow. 24 strains that grew at 42° C. were isolated. Plasmids were prepared and tested for complementation in KS419. 13 strains contained plasmids that complemented KS419 for growth at 42° C.

As a second check for the presence of the deqP gene the plasmids were tested to observe whether they will restore proteolysis of Tsr AP2 in a deqP mutant. The pKS3 plasmid (encoding Tsr-AP2) and the above described Mud4042 plasmids have different plasmid origins of replication and are thus compatible with each other in bacterial strains. Thus, pKS3 can be introduced into strains having the Mud4042 plasmids. Three of the Mud4042 plasmids (pKS9, 10 and 11) when tested in deqP mutant expressing Tsr-AP2, restored AP halos on agar plates. Those three were also tested by osmotic shock and AP assay. All three restored degradation of Tsr-AP2 by this assay, as shown in Table 3.

TABLE 3

| Chromosome | Plasmid | Osmotic Shock Alkaline Phosphatase | | Total Unit |
|---|---|---|---|---|
| degP | | Shocked Cells | Shock Fluid | |
| | | (membrane & cytoplasm) | (periplasm) | |
| + | pKS1(Tsr-AP1) | 96% | 4% | 1695 |
| + | pKS3(Tsr-AP2) | 46 | 54 | 653 |
| − | pKS1(Tsr-AP1) | 93 | 7 | 1501 |
| − | pKS3(Tsr-AP2) | 96 | 4 | 924 |
| − | pKS3(Tsr-AP2) pKS5(Mud:proAB) | 94 | 6 | 471 |
| − | pKS3(Tsr-AP2) pKS9(Mud:degP) | 43 | 57 | 806 |
| − | pKS3(Tsr-AP2) pKS10(Mud:degP) | 35 | 65 | 423 |
| − | pKS3(Tsr-AP2) pKS11(Mud:degP) | 37 | 63 | 724 |

Restriction digests of pKS9, 10 and 11 show that pKS9 and 11 have no BamHI or HindIII sites in the deqP insert, and that pKS10 has one BamHI and one HindIII site in the insert; those sites must not be within deqP since they are not present in pKS9 and 11. The restriction map of BamHI and HindIII sites in Mud4042 shows that these sites are close to the ends of Mud4042. Consequently, most of the Mud4042 sequences can be eliminated by subcloning the deqP inserts with HindIII and BamHI. pKS9, 10 and 11 all contain 2 common PstI fragments (1.35 kb and 0.95 kb), therefore these three plasmids do contain inserts derived from one region of the chromosome.

Subclones of a BamHI - BamHI fragment from pKS10 into pACYC184 were constructed which complement the degP4::Tn5 mutation. With the fragment cloned in one orientation (pKS12, FIG. 4) this plasmid does not noticeably affect cell growth. In the opposite orientation (pKS13) cell growth is very slow in both degP+ and degP− host cells.

Figure 4:
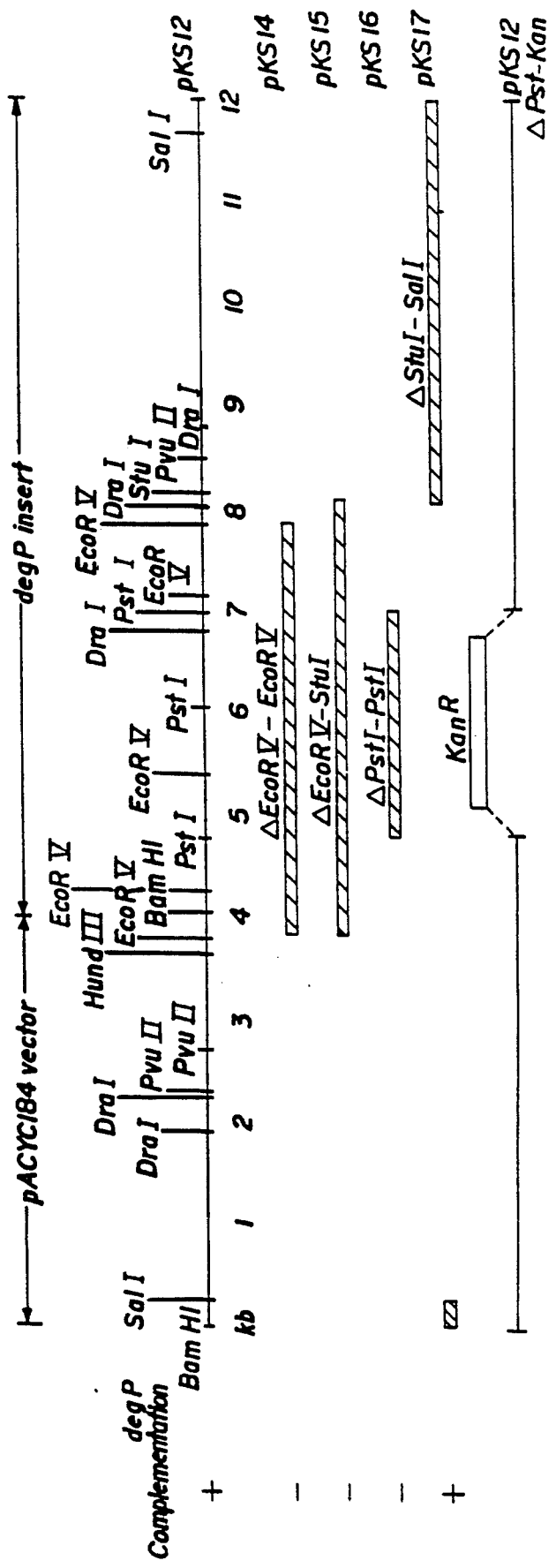
FIG. 4 is a restriction endonuclease map and deletion map of pKS12 and derivative plasmids.

Deletions were made on pKS12 by standard procedure, and are shown in FIG. 4. Complementation of degP− by these plasmids was assayed by osmotic shock and AP activity; the results are shown in Table 4. pKS12 and 17 are the only two of these plasmids to complement degP; the other plasmids are deleted for at least a part of the degP gene.

TABLE 4

| Chromosome degP | Tsr-AP | Plasmid | % Alkaline Phosphatase | |
|---|---|---|---|---|
| | | | Shocked Cells | Shock Fluid |
| + | 1 | pACYC184 | 97 | 3 |
| + | 2 | pACYC184 | 34 | 66 |
| − | 1 | pACYC184 | 95 | 5 |
| − | 2 | pACYC184 | 98 | 2 |
| + | 2 | pKS12 | 37 | 63 |
| − | 2 | pKS12 | 38 | 62 |
| − | 2 | pKS14 | 99 | 1 |
| − | 2 | pKS15 | 95 | 5 |
| − | 2 | pKS16 | 88 | 12 |
| − | 2 | pKS17 | 37 | 63 |

EXAMPLE 4

CONSTRUCTION OF DEGP DELETION MUTANT

A deletion mutant of pKS12 was constructed and recombined into the chromosome of E. coli. Its location was then determined to compare the location of the gene insert to the location of degP4::Tn5.

pKS16 (a ΔPstI-PstI plasmid, shown in FIG. 4) does not complement deqP+. This deletion is contained within the deqP insert in pKS12. Therefore, it has homology outside the deletion for recombination into the chromosome. A derivative of pKS12 was constructed in which the two PstI fragments were deleted and a selectable marker (Kanamycin resistance) was inserted in their place. This construction entailed digestion of pKS12 and pUC-4K (Vierra et al. 19 Gene 259, 1982) with PstI, ligation and transformation into E. coli, selecting Kan$^r$ Cam$^r$. Constructs of pKS12 having a 1.4kb (see FIG. 4) PstI fragment inserted from pUC-4K in one of both orientations were taken and used to recombine into the E. coli chromosome as follows, the Plasmids are termed DKS12 ΔPst-Kan.

The pKS12 ΔPst Kan plasmids were transformed into Hfr cells (Thr+Pro+Str$^s$Kan$^s$Cam$^s$) selecting Kan$^r$ Cam$^r$. Some of these cells may have the plasmid integrated by homologous recombination into the chromosome of the Hfr strain, near the deqP gene. Because only chromosomally integrated plasmids can be transferred to recipients in Hfr matings, these integrated plasmids can be identified by mating the Hfr cells to recipient F− cells (Thr−ProAB−Str$^R$) and selecting Thr+Pro+Kan$^r$Str$^s$. To identify cells in which a second recombination has deleted the plasmid sequences and the deqP+ gene and retained the degPΔPst-Kan gene on the chromosome, a P1 transduction was carried out.

50–100 colonies from the Hfr cross were pooled and grown with P1 transducing phage. This phage was used to transduce a deqP+ strain KS272 to Kan$^r$ and the resulting colonies were screened for Cam$^s$. These cells are the product of a recombination event which deletes the deqP+ gene of the host cell and replaces it with the deqP deletion fragment and the Kan$^R$ gene; other plasmid fragments are also removed. Thus, this Cam$^s$ strain is deleted for deqP, and has a Kan$^r$ marker in its place. This process causes the ΔPst-Kan to be recombined into the chromosome. Two mutations were isolated and termed deqP41 and deqP44. The Kan$^r$ of each mutation was mapped by P1 transduction, using P1 grown on a strain carrying zad-339::Tn10 (80% linked by P1 transduction to deqP). These two mutations show the same linkage to zad-339::Tn10 as does deqP4::Tn5. Thus, the chromosomal insert in pKS12 appears to correspond to the locus of the deqP4::Tn5 mutation, and contains the deqP gene.

Deposit

E. coli strain KS334, containing mutation K4 (having a defective periplasmic protease and containing a pBR322 plasmid (pKS3) having the alkaline phosphatase-Tsr fusion 2) has been deposited with the American Type Culture Collection (ATCC), and assigned the number 53583. It was deposited on 1/28/87.

E. coli strain KS440 containing plasmid pKS12 (having DNA encoding the deqP gene) has been deposited with the ATCC and assigned the number 67488. It was deposited on August 4, 1987.

Applicants' assignee, President and Fellows of Harvard College, acknowledge their responsibility to replace these cultures should they die before the end of the term of a patent issued hereon, 5 years after the last request for a culture, or 30 years, whichever is the longer, and their responsibility to notify the depository of the issuance of such a patent, at which time the deposit will irrevocably be made available to the public. Until that time the deposit will be made available to the Commissioner of Patents under the terms of 37 CFR Section 1-14 and 35 USC Section 112.

Other embodiments are within the following claims.

I claim:

1. A method of isolating a mutant strain of *Escherichia coli* having a defective periplasmic protease, said method comprising the steps of:
   mutagenizing an *E. coli* cell, said cell comprising:
   (a) an inner and an outer membrane,
   (b) a periplasmic space between said membranes,
   (c) a protein which in a first state is mobile, being able to move through said outer membrane and enter medium surrounding said cell, and in a second state is not mobile, remaining inside said cell, said protein in said first state being detectable in said medium, and
   (d) a periplasmic protease which converts said protein from said second state to said first state in said cell, and
   selecting and isolating a mutant cell which produces when in said medium a reduced level of said detectable protein in said medium compared to the level of said detectable protein produced by said non-mutagenized *E. coli* cell when suspended in an identical medium, which mutant cell comprises a periplasmic protease having a reduced ability, compared to the corresponding *native* periplasmic protease in said *E. coli* cell, to degrade abnormal or foreign proteins.

2. The method of claim 1 wherein said protein is detected by (a) measuring the enzymatic activity of said protein in said medium, or (b) detecting reactivity of said protein in said medium with a specific antibody to said protein.

3. The method of claim 1 wherein said selecting and isolating step comprises screening a plurality of said mutagenized cells by culturing said cells and testing each resulting culture or colony for said detectable protein.

4. The method of claim 1 wherein said protein comprises a fusion of a first polypeptide chain which is susceptible to proteolysis by said periplasmic protease, and a second polypeptide chain which has a detectable enzymatic activity and is not susceptible to proteolysis by said protease.

5. The method of claim 4 wherein said first polypeptide chain comprises at least 20 contiguous amino acids of Tsr.

6. The method of claim 4 wherein said second polypeptide chain comprises a portion of alkaline phosphatase from *E. coli*, said portion having an enzymatic activity of alkaline phosphatase.

7. The method of claim 1 wherein said protein in said second state has a half-life of less than 60 minutes in said cell having a native periplasmic protease and said half-life is greater than 60 minutes in said cell having a defective protease.

8. The method of claim 1 wherein said protein in said second state is bound to one of said inner and outer membranes.

9. The method of claim 1 wherein said cell comprises a mutation resulting in said cell allowing said protein to move through said outer membrane.

10. A mutant strain of *E. coli* having a mutant periplasmic protease with a reduced level of protease activity compared to the corresponding naturally occurring protease, wherein the naturally occurring form of said protease has proteolytic activity on a protein of at least 10 kD and at sites at least about 30 amino acids from the amino-terminus of said protein, said mutant periplasmic protease having a reduced ability, compared to said naturally occurring protease, to degrade abnormal or foreign proteins.

11. The strain of claim 10 wherein said strain is isolated by mutagenizing an *E. coli* cell, wherein said cell comprises an inner and an outer membrane, a periplasmic space between said membranes, a protein which in a first state is mobile, being able to move through said outer membrane and enter medium surrounding said cell, and in a second state is not mobile, remaining inside said cell, said protein in said first state being detectable in said medium, and a periplasmic protease which converts said protein from said second state to said first state in said cell, and
   selecting and isolating a mutant cell which produces when suspended in said medium a reduced level of said detectable protein in said medium compared to the level of said detectable protein produced by said non-mutagenized *E. coli* cell, when suspended in an identical medium.

12. The strain of claim 10 or 11 wherein said mutant cell is strain KS334.

13. The method of claim 1 wherein said protein in said second state has a half-life of less than 60 minutes in said cell having a native periplasmic protease and said half-life in said cell having a defective protease is greater than said half-life in said cell with native protease.

14. A cell of *E. coli* having a first mutation in a game encoding a periplasmic protease, wherein the genetic map position of said gene is located within 1 minute of mutation K4, and wherein said first mutation reduces the level of protease activity of said protease.

15. The cell of claim 14 wherein said gene is linked by P1 transduction to pan or fhuAB (tonA).

16. The cell of claim 14 wherein said gene is located at a map position of about four minutes on the *E. coli* chromosome.

17. The cell of claim 14 wherein said gene is present on the plasmid pKS12, contained in deposit ATCC67488.

18. The cell of claim 14 wherein said mutation is a deletion mutation.

19. The cell of claim 18 wherein said mutation is a deletion of a part of degP.

20. The cell of claim 14 wherein said mutation is degP41 or degP44.

* * * * *

UNITED STATES PATENT AND TRADEMARK OFFICE
CERTIFICATE OF CORRECTION

PATENT NO. : 4,946,783

DATED : August 7, 1990

INVENTOR(S) : Beckwith et al.

It is certified that error appears in the above-identified patent and that said Letters Patent is hereby corrected as shown below:

Col. 2, line 55; "deqP41 or deqP44" should be --degP41 or degP44--.
Col. 2, line 54; "deqP" should be --degP--.
Col. 3, line 25; insert --features detection of cells having defective periplasmic-- after "invention".
Col. 5, line 16; insert a hyphen between "Tsr alkaline".
Col. 5, line 36; delete the spaces before "100-200".
Col. 5, line 42; insert --no-- after "have".
Col. 5, line 66; insert a hyphen between "membrane bound".
Col. 6, line 10; insert --mutations-- before "derived".
Col. 6, line 15; "alkaling" should be --alkaline--.
Col. 6, line 35; "unlabeled" should be --unlabelled--.
Col. 7, line 43; insert a hyphen between "Tsr alkaline".
Col. 7, line 46; insert a hyphen between "Tsr alkaline".
Col. 8, line 38; insert --)-- after "(16 Pan$^+$".
Col. 8, line 41; insert --)-- after "(132$\phi$80$^s$".
Col. 8, line 48; "deqP4" should be --degP4--.
Col. 8, line 50; insert a hyphen between "Tsr AP2".
Col. 8, line 54; "deqP4" should be --degP4--.
Col. 8, line 63; change "plasmids." to --plasmids,--.
Col. 8, line 67; "malT$^C$1 deqP4::Tn5(Mu)" should be --malT$^C$-1 degP4::Tn5(Mu$^+$).
Col. 9, lines 3, 7, 9, 16, 44, 46, and 50; "deqP" should be "degP".
Col. 9, line 9; insert a hyphen between "Tsr AP2".

UNITED STATES PATENT AND TRADEMARK OFFICE
CERTIFICATE OF CORRECTION

PATENT NO. : 4,946,783

DATED : August 7, 1990

INVENTOR(S) : Beckwith et al.

It is certified that error appears in the above-identified patent and that said Letters Patent is hereby corrected as shown below:

```
Col. 9, line 25; insert --)-- after "(membrane & cytoplasm".
Col. 10, lines 42, 43, 60 and 67; "deqP" should be --degP--.
Col. 10, line 54; "Plasmids" should be --plasmids--.
Col. 10, line 55; "DKS12" should be --pKS12--.
Col. 11, line 12; "deqP41 and deqP44" should be --degP41 and degP44--.
Col. 13, line 5; "game" should be --gene--.
```

Signed and Sealed this

Twenty-fifth Day of August, 1992

Attest:

DOUGLAS B. COMER

Attesting Officer

Acting Commissioner of Patents and Trademarks